United States Patent [19]

Dusza et al.

[11] Patent Number: 5,059,709
[45] Date of Patent: Oct. 22, 1991

[54] PROCESS FOR THE SYNTHESIS OF α-[(DIALKYLAMINO)SUBSTITUTED-METHYLENE]-β-OXO-(SUBSTITUTED)PROPANENTRILES

[75] Inventors: John P. Dusza, Nanuet, N.Y.; Robert F. Church, Cos Cob, Conn.

[73] Assignee: American Cyanamid Company, Stamford, Conn.

[21] Appl. No.: 613,601

[22] Filed: Nov. 13, 1990

[51] Int. Cl.$^5$ ............................................. C07C 253/00
[52] U.S. Cl. ................................. 558/309; 558/303; 558/308; 558/311; 558/312; 558/313; 558/315; 548/240; 548/243; 548/244
[58] Field of Search ................. 558/308, 309, 315, 312

[56] References Cited

U.S. PATENT DOCUMENTS

| | | | |
|---|---|---|---|
| 4,178,449 | 12/1979 | Dusza et al. | 544/281 |
| 4,236,005 | 11/1980 | Dusza et al. | 544/281 |
| 4,281,000 | 7/1981 | Dusza et al. | 424/251 |
| 4,521,422 | 6/1985 | Dusza et al. | 514/258 |
| 4,900,836 | 2/1990 | Tomcufcik et al. | 546/279 |

*Primary Examiner*—Jose G. Dees
*Assistant Examiner*—Barbara Stuckey
*Attorney, Agent, or Firm*—Thomas S. Szatkowski

[57] ABSTRACT

A novel process for producing α-[(dialkylamino) substituted-methylene]β-oxo-(substituted) propanenitriles of the formula:

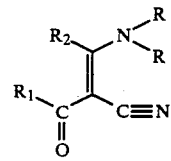

where R, $R_1$ and $R_2$ are defined in the specification by reacting a substituted isoxazole with a diaklylamide dimethylacetal is provided.

19 Claims, No Drawings

PROCESS FOR THE SYNTHESIS OF α-[(DIALKYLAMINO)SUBSTITUTED-METHYLENE]-β-OXO-(SUBSTITUTED)PROPANENTRILES

BACKGROUND OF THE INVENTION

1. Field of the Invention

The invention relates to a process for the synthesis of α-[(dialkylamino)substituted methylene]-β-oxo-(substituted)propanenitrile compounds and to novel substituted isoxazole compounds useful as intermediates in the process.

2. Description of the Prior Art

The α-[(dialkylamino)substituted-methylene]-β-oxo-(substituted)propanitrile compounds are important intermediates for the preparation of therapeutic aryl and heteroaryl [7-(aryl and heteroaryl)pyrazolo(1,5-a)-pyrimidin-3-yl]methanone compounds which are useful as anxiolylic, antiepileptic, sedative-hypnotic and skeletal muscle relaxant agents. The aryl and heteroaryl [7-(aryl and hetroaryl)-pyrazolo [1,5-a] pyrimidin-3-yl]methanone compounds and uses for such compounds are described in U.S. Pat. No. 4,521,422, the contents of which are incorporated by reference.

In U.S. Pat. No. 4,900,836, the contents of which are incorporated by reference, a series of reactions in which the α-[(dialkylamino)substituted methylene]-β-oxo-(substituted)propanenitrile compounds are utilized to produce the [7-(alkyl and hetroaryl)pyrazolo (1,5-a)-pyrimidin-3-yl]methanone compounds is described. This reference also describes the synthesis of the α-[(dialkylamino) substituted methylene]-β-oxo-(substituted) propanenitrile compounds via the reaction of a substituted acetonitrile with a dimethylformamide dimethylacetal.

It has now been found that α-[(dialkylamino) substituted methylene]β-oxo-(substituted) propane nitrile compounds may be advantageously synthesized via reaction of a substituted isoxazole with a dialkylamide dimethylacetal. The use of substituted isoxazole compounds in the production of α-[(dialkylamino)substituted methylene]-β-oxo(substituted)propanenitrile compounds has not been taught nor suggested by the art.

Certain substituted isoxazole compounds and their synthesis are known. For example, 5-(2,3,4,5-tetrafluorophenyl)-isoxazole (Chem. Abst. Registry No. 110985-65-4), 5-(2,4-dichloro-5-fluorophenyl) isoxazole (Registry No. 103318-74-6), 5-(2,3,-dichloro-phenyl) isoxazole (Registry No. 76344-98-4), 5-(5-nitro-2-furyl)-isoxazole (Registry No. 32332-91-5), 5-(4-methyl-phenyl)-isoxazole (Registry No. 7064-35-9), 5-(m-chloro phenyl) isoxazole (Registry No. 7064-34-8), 5-(m-bromo phenyl) isoxazole (Registry No. 7064-33-7), 5-(p-chloro-phenyl) isoxazole (Registry No. 7064-32-6), 5-(p-bromo phenyl) isoxazole (Registry No. 7064-31-5), N-[[(4,6-dimethoxy-2-pyrimidinyl)amino]carbonyl]-2-5-isoxazolyl)-3-thiophenesulfonamide (Registry No. 103118-33-8), 3-hydroxy-4-(5-isoxazolyl)-2(5H)-foranone (Registry No. 84-608-81-1) and 5-phenyl isoxazole (Registry No. 1006-67-3) are known. Other substituted isoxazole compounds including those claimed herein are not known.

SUMMARY OF THE INVENTION

The invention provides an improved process for the large scale production of α-[(dialkylamino)substituted-methylene]-β-oxo-(substituted)propanitrile compounds which may be represented by the following structural formula:

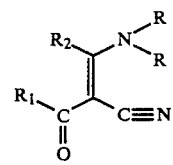

wherein R is lower alkyl($C_1$–$C_3$); $R_1$ is selected from the group consisting of phenyl; phenyl substituted by one of the group selected from halogen, nitro, alkyl($C_1$–$C_3$) and alkoxy($C_1$–$C_3$); phenyl di- or trisubstituted by methoxy, halogen and lower alkyl; phenyl substituted by one of the group consisting of dialkylamino($C_1$–$C_3$), methylenedioxy, alkylthio($C_1$–$C_3$), alkylsulfonyl($C_1$–$C_3$), amino, alkanoyl($C_1$–$C_3$), amino, trifluoromethyl and phenyl; thienyl; thienyl substituted by one or two of the group selected from halogen and alkyl($C_1$–$C_3$); furanyl; furanyl substituted by one or two of the group selected from alkyl($C_1$–$C_3$), naphthalenyl, pyrazinyl, and pyrrolyl; and $R_2$ is selected from the group consisting of hydrogen and lower alkyl ($C_1$–$C_3$). The improved process comprises reacting an $R_1$ substituted isoxazole having the formula

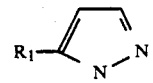

wherein $R_1$ is as defined above with a dialkylamide dimethylacetal having the formula

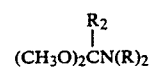

wherein R and $R^2$ are as defined above at a temperature from about 50° C. to about 100° C. and recovering the α-[(dialkylamino)substituted methylene]-β-oxo-(substituted) propanenitrile so produced. The invention also provides certain novel $R_1$ substituted isoxazole compounds.

DESCRIPTION OF THE PREFERRED EMBODIMENTS

The process and compounds of the present invention are described in the following reaction scheme I:

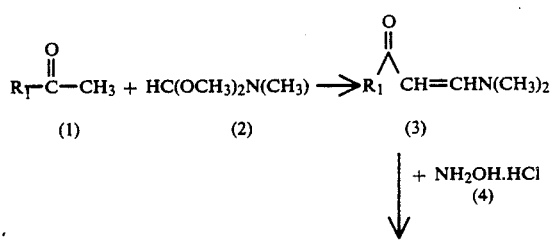

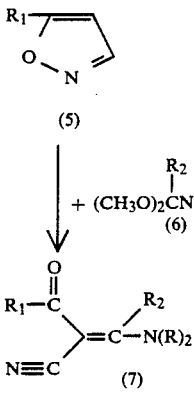

In accordance with the above reaction scheme a 1-(cyclicsubstituted)ethanone (1), where $R_1$ is as described above, is reacted with dimethylformamide dimethyl acetal (2) for 15 hours at 50°-100° C. Evaporation and recrystallization gives the 3-dimethylamino-1-(substituted)-2-propen-1-one (3).

The 3-dimethylamino-1-(substituted)-2-propen-1-one compounds (3) and their synthesis are described in greater detail in U.S. Pat. No. 4,178,449 (col 2 lines 44-54), U.S. Pat. No. 4,281,000 (col 2 lines 28-34), and U.S. Pat. No. 4,236,005 (col 2 lines 45-54).

The 3-dimethylamino-1-(substituted)-2-propen-1-one (3) is reacted with hydroxylamine hydrochloride in absolute methanol for 2 hours at a temperature from about 50° to about 100° C. The reaction solution is evaporated, dissolved in methylene chloride and passed thru hydrous magnesium silicate. Concentration of the eluate gives the desired substituted isoxazole (5) which is reacted with a dialkylamide dimethylacetal (6) at a temperature from about 50° to about 100° C. for 4 hours. The reaction solution is evaporated, dissolved in methylene chloride and passed thru hydrous magnesium silicate. On cooling and/or concentrating the methylene chloride solution, the desired α-[(dialkylamino)substituted methylene]-β-oxo-(substituted) propanenitrile (7) crystallizes.

As described in U.S. Pat. No. 4,900,836, the α[(dialkylamino)substituted methylene]-β-oxo-(substituted)-propanenitriles find utility as intermediates in the preparation of therapeutic aryl and heteroaryl[7-(aryl and heteroaryl)pyrazolo(1,5-a)pyrimidin-3-yl] methanones. As described in U.S. Pat. No. 4,521,422 the aryl and heteroaryl [7-(aryl and heteroaryl)pyrazolo(1,5-a) pyrimidin-3-yl]methanones are useful as anxiolylic, antiepileptic, sedative-hypnotic, and skeletal muscle relaxant agents.

The above described process is an improvement over the procedure described in U.S. Pat. No. 4,900,836. The 1-(cyclicsubstituted)ethanones are readily available and inexpensive; the over all yields are higher; and the reaction work-ups are less labor and time intensive.

The following non-limiting examples illustrate the process of the present invention as well as the preparation of the novel compounds isoxazole intermediates.

EXAMPLE 1

3-Dimethylamino-1-(3-thienyl)-2-propen-1-one

A mixture of 48.4 g of 3-acetylthiophene and 75 ml of dimethylformamide dimethyl acetal, under nitrogen, is heated for 15 hours on a steam bath. The reaction is concentrated in vacuo and the residue crystallized from methylene chloride/hexane to give 60.55 g (87%) of the desired product, mp 89°-90° C.

Using the general procedure of Example 1, the following compounds of Example 2-26 shown in Table 1 are prepared.

TABLE I

| Example | Starting Material | Compound | MP °C. |
|---|---|---|---|
| 2 | Acetophenone | 3-dimethylaminoacrylophenone | 93.0-94° |
| 3 | 2-Acetyl-5-bromothiophene | 1-(5-bromo-2-thienyl)-3-dimethylamino-2-propen-1-one | 118-120° |
| 4 | 4'-Chloroacetophenone | trans-4'-chloro-3-dimethylaminoacrylophenone | 83-84° |
| 5 | 4'-Methoxyacetophenone | 3-dimethylamino-4'-methoxyacrylophenone | 92-95° |
| 6 | 4'-Methylacetophenone | 3-dimethylamino-4'-methylacrylophenone | 92.5-95° |
| 7 | 2-Acety-5-methylthiopene | 1-(5-methyl-2-thienyl)-3-dimethylamino-2-propen-1-one | 113-115° |
| 8 | 2-Acetylfuran | 3-(dimethylamino)-1-(2-furyl)-2-propen-1-one | 84-86° |
| 9 | 2-Acetyl-5-methylfuran | 3-(dimethylamino)-1-(5-methyl-2-furanyl)-2-propen-1-one | 126-128° |
| 10 | 3'-Ethylacetophenone | 3-(dimethylamino)-1-(3-ethylphenyl)-2-propen-1-one | yellow orange viscous liquid |
| 11 | 4'-Nitroacetophenone | 3-dimethylamino-4'-nitroacrylophenone | 150-151° |
| 12 | 2'-Fluoroacetophenone | (E)-3-dimethylamino-2'-fluoroacrylophenone | yellow oil |
| 13 | 4'-Fluoroacetophenone | trans-3-dimethylamino-4'-fluoroacrylophenone | 96-97° |
| 14 | 1-Adamanyl methyl ketone | 3-dimethylamino-1-tricyclo[3.3.1.1$^{3,7}$]-dec-1-yl-2-propen-1-one | 142-143° |
| 15 | 4'-Acetylbiphenyl | 3-dimethylamino-4'-phenylacrylophenone | 135-137.5° |
| 16 | 2'-Acetonaphthone | (E)-3-dimethylamino-2'-acrylonaphthone | 96-98° |
| 17 | 3',4'-Dichloroacetophenone | trans-3',4'-dichloro-3-dimethylamino-acrylophenone | 94-95° |
| 18 | 3',4'-Dimethylacetophenone | 3-dimethylamino-3',4'-dimethylacrylophenone | 108-110° |
| 19 | 2',4'-Dichloroacetophenone | 2',4'-Dichloro-3-dimethylaminoacrylophenone | 83.5-85° |
| 20 | 2',6'-Difluoroacetophenone | 1'-(2',6'-difluorophenyl)-3-(dimethylamino)-2-propen-1-one | 67-69° |
| 21 | 2-Acetyl-4-methylthiophene | 3-(dimethylamino)-1-(4-methyl-2-thienyl)-2-propen-1-one | 102-104° |
| 22 | 3-Acetyl-1-methylpyrrole | 3-(dimethylamino)-1-(1-methyl-1H-pyrrol-3-yl)-2-propen-1-one | 123-125° |

TABLE I-continued

| Example | Starting Material | Compound | MP °C. |
|---|---|---|---|
| 23 | 2-Acetylthiophene | 3-dimethylamino-1-(2-thienyl)-2-propen-1-one | 114–115° |
| 24 | 2-Acetyl-3-methylthiophene | (E)-3-dimethylamino-1-(3-methyl-2-thienyl)-2-propen-1-one | 45–49° |
| 25 | 2',4'-Difluoroacetophenone | 3-dimethylamino-2',4'-difluoroacrylophenone | 48–49° |
| 26 | 2',5'-Difluoroacetophenone | 3-dimethylamino-2',5'-difluoroacrylophenone | 66–67° |

EXAMPLE 27

A mixture of 58.1 g of (3-dimethylamino-1-(3-thienyl)-2-propen-1-one, 23.4 g of hydroxylamine hydrochloride and 250 ml of commercial absolute methanol is heated on a steam bath for 2 hours. The reaction is concentrated in vacuo, partitioned between methylene chloride and water and the organic layer dried over sodium sulfate. The methylene chloride is passed thru a short column of hydrous magnesium silicate and concentrated in vacuo to give 41.25 g (85%) of the desired product as a red-orange oil which solidified on standing. CI-MS: M/z 151(M+).

Using the general procedure of Example 27, the following compounds of Example 28–52, shown in Table II are prepared.

TABLE II

| Example | Starting Material of Example | Compound | MP °C. |
|---|---|---|---|
| 28 | 2 | 5-Phenylisoxazole | Colorless liquid |
| 29 | 3 | 5-(5-Bromo-2-thienyl)-isoxazole | 66–68° |
| 30 | 4 | 5-(p-Chlorophenyl)-isoxazole | 84–85° |
| 31 | 5 | 5-(p-Methoxyphenyl)-isoxazole | 64–65° |
| 32 | 6 | 5-p-Tolylisoxazole | 60–61° |
| 33 | 7 | 5-(5-Methyl-2-thienyl)-isoxazole | 30–32° |
| 34 | 8 | 5-(2-Furanyl)isoxazole | Pale yellow oil |
| 35 | 9 | 5-(5-Methyl-2-furanyl)-isoxazole | 32–33° |
| 36 | 10 | 5-(3-Ethylphenyl)isoxazole | Colorless liquid |
| 37 | 11 | 5-(4-Nitrophenyl)isoxazole | 172–174° |
| 38 | 12 | 5-(2-Fluorophenyl)isoxazole | Yellow liquid |
| 39 | 13 | 5-(4-Fluorophenyl)isoxazole | 52–53° |
| 40 | 14 | 5-Tricyclo[3.3.1.1.$^{3,7}$]-dec-1-yl-isoxazole | 32–33° |
| 41 | 15 | 5-[1,1'-Biphenyl]-4-yl-isoxazole | 130–132° |
| 42 | 16 | 5-(2-Naphthalenyl)isoxazole | 110–112° |
| 43 | 17 | 5-(3,4-Dichlorophenyl)-isoxazole | 88–89° |
| 44 | 18 | 5-(3,4-Dimethylphenyl)-isoxazole | 46–47° |
| 45 | 19 | 5-(2,4-Dichlorophenyl)-isoxazole | 127–129° |
| 46 | 20 | 5-(2,6-Difluorophenyl)-isoxazole | 63–64° |
| 47 | 21 | 5-(4-Methyl-2-thienyl)-isoxazole | pale yellow liquid |
| 48 | 22 | 5-(1-Methyl-1H-pyrrol-2-yl)isoxazole | pale yellow liquid |
| 49 | 23 | 5-(2-Thienyl)isoxazole | dark yellow-orange liquid |
| 50 | 24 | 5-(3-Methyl-2-thienyl)-isoxazole | pale yellow liquid |
| 51 | 25 | 5-(2,4-Difluorophenyl)-isoxazole | 64–66° |
| 52 | 26 | 5-(2,5-Difluorophenyl)-isoxazole | 74–77° |

EXAMPLE 53

α-[(Dimethylamino)methylene]-β-oxo-3-thiophenepropanenitrile

A mixture of 41.2 g of 5-(3-thienyl)isoxazole and 36.0 g of dimethylformamide dimethylacetal, under nitrogen, is heated on a stream bath for 4 hours. The reaction is concentrated in vacuo to give a viscous oil which solidified. The residue is dissolved in methylene chloride and passed thru a short column of hydrous magnesium silicate. On cooling, 31.76 g of the desired product is obtained, mp 118°–119°, CI-MS:m/z 206(M$^{30}$). Concentrating in vacuo the methylene chloride gives an additional 20.2 g of product. (Total recovered 51.96 g, 92%).

Using the general procedure of Example 53, the following compounds of Example 54–78, shown in Table III are prepared.

TABLE III

| Example | Starting Material of Example | Compound | MP °C. |
|---|---|---|---|
| 54 | 28 | 2-Benzoyl-3-dimethyl-aminoacrylonitrile | 111–113° |
| 55 | 28 | 5-Bromo-α-[(dimethyl-amino)methylene]-β-oxo-2-thiophenepropanenitrile | 190–192° |
| 56 | 29 | 2-p-Chlorobenzoyl-3-dimethylaminoacrylonitrile | 118–121° |
| 57 | 30 | α-[(Dimethylamino)methylene]-4-methoxy-β-oxo-benzenepropanenitrile | 107–110° (dec) |
| 58 | 31 | α-[(Dimethylamino)methylene]-4-methyl-β-oxo-benzenepropanenitrile | 132–135° |
| 59 | 32 | α-[(Dimethylamino)methylene]-5-methyl-β-oxo-2-thiophenepropanenitrile | 151–153° |
| 60 | 33 | α-[(Dimethylamino)methylene]-β-oxo-2-furanpropanenitrile | 112–115° |
| 61 | 34 | α-[(Dimethylamino)methylene]-5-methyl-β-oxo-2-furanpropanenitrile | 135–137° |
| 62 | 35 | α-[(Dimethylamino)methylene]-3-ethyl-β-oxo-benzenepropanenitrile | red-orange oil |
| 63 | 36 | α-[(Dimethylamino)methylene]-4-nitro-β-oxo-benzenepropanenitrile | 154–156° |
| 64 | 37 | α-[(Dimethylamino)methylene]-2-fluoro-β-oxo-benzenepropanenitrile | 62–74° |
| 65 | 38 | α-[(Dimethylamino)methy- | 142–145° |

TABLE III-continued

| Example | Starting Material of Example | Compound | MP °C. |
|---|---|---|---|
| 66 | 39 | lene]-4-fluoro-β-oxo-benzenepropanenitrile α-[(Dimethylamino)methylene]-β-oxo-tricyclo-[3.3.1.1.³,⁷]decane-1-propanenitrile | 183–189° |
| 67 | 40 | α-[(Dimethylamino)methylene]-β-oxo-4-biphenyl-propionitrile | 174–176° |
| 68 | 41 | α-[(Dimethylamino)methylene]-β-oxo-2-naphthalene-propanenitrile | 115–118° |
| 69 | 42 | 3,4-Dichloro-α-[(dimethylamino)methyl]-β-oxo-benzenepropanenitrile | 130–142° |
| 70 | 43 | α-[(Dimethylamino)methylene]-3,4-dimethyl-β-oxo-benzenepropanenitrile | 82–112° |
| 71 | 44 | 2,4-Dichloro-α-[(dimethylamino)methylene]-β-oxo-benzenepropanenitrile | yellow glass |
| 72 | 45 | α-[(Dimethylamino)methylene]-2,6-difluoro-β-oxo-benzenepropanenitrile | 109–111° |
| 73 | 46 | α-[(Dimethylamino)methylene]-4-methyl-β-oxo-2-thiophenepropanetrile | 127–132° |
| 74 | 47 | α-[(Dimethylamino)methylene]-1-methyl-β-oxo-1H-pyrrole-2-propanenitrile | 97–100° |
| 75 | 48 | α-[(Dimethylamino)methylene]-β-oxo-2-thiophenepropanenitrile | 136–140° |
| 76 | 49 | α-[(Dimethylamino)methylene]-3-methyl-β-oxo-2-thiophenepropanenitrile | red-brown viscous syrup |
| 77 | 50 | α-[(Dimethylamino)methylene]-2,4-difluoro-β-oxo-benzenepropanenitrile | 137–139° |
| 78 | 51 | α-[(Dimethylamino)methylene]-2,5-difluoro-β-oxo-benzenepropanenitrile | 108–110° |

We claim:

1. A process for producing compounds of the formula:

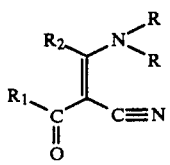

wherein R is lower alkyl ($C_1$–$C_3$); $R_1$ is selected from the group consisting of phenyl substituted by one of the group selected from halogen, nitro, alkyl($C_1$–$C_3$) and alkoxy($C_1$–$C_3$); phenyl di- or tri- substituted by methoxy, halogen and lower alkyl; phenyl substituted by one of the group consisting of dialkylamino($C_1$–$C_3$), methylenedioxy, alkylthio($C_1$–$C_3$), alkylsulfonyl(-$C_1$–$C_3$)-amino, alkanoyl ($C_1$–$C_3$)amino, trifluoromethyl and phenyl; thienyl; thienyl substituted by one or two of the group selected from halogen and alkyl($C_1$–$C_3$); furanyl; furanyl substituted by one or two of the group selected from alkyl($C_1$–$C_3$), naphthalenyl, pyrazinyl and pyrrolyl; and $R_2$ is selected from the group consisting of hydrogen and lower alkyl($C_1$–$C_3$); which comprises:

reacting a substituted isoxazole having the formula

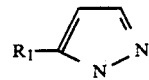

with dialkylamide dimethylacetal having the formula

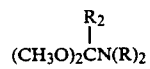

at a temperature from about 50° to about 100° C. and recovering the α-[(dialkylamino)substituted methylene]-β-oxo-(substituted)propanenitrile so produced.

2. The process of claim 1, wherein said substituted isoxazole is prepared by reacting a 3-dimethylamino-1-substituted-2-propen-1-one having the formula

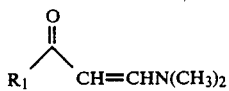

with hydroxylamine hydrochloride in absolute methanol at a temperature from about 50° C. to about 100° C.

3. The process of claim 2 wherein said 3-dimethylamino-1-substituted 2-propen-1-one is prepared by reacting a 1-(cyclic substituted) ethanone having the formula

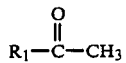

with dimethylformamide dimethylacetal at a temperature of from about 50° C. to about 100° C.

4. The process of claim 1, wherein α-[(dimethylamino)methylene]-β-oxo-3-thiophenepropanenitrile is produced.

5. The process of claim 1, wherein 5-bromo-α-[(dimethylamino)methylene]-β-oxo-2-thiophenepropanenitrile is produced.

6. The process of claim 1, wherein α-[(dimethylamino)methylene]-5-methyl-β-oxo-2-furanpropanenitrile is produced.

7. The process of claim 1, wherein α-[(dimethylamino)methylene]-3-ethyl-β-oxo-benzenepropanenitrile is produced.

8. The process of claim 1, wherein α-[(dimethylamino)methylene]-4-nitro-β-oxo-benzenepropanenitrile is produced.

9. The process of claim 1, wherein α-[(dimethylamino)methylene]-β-oxo-tricyclo[3.3.1.1³,⁷]-decane-1-propanenitrile is produced.

10. The process of claim 1, wherein α-[(dimethylamino)methylene]-β-oxo-4-biphenylpropanenitrile is produced.

11. The process of claim 1, wherein 3,4-dichloro-α-[(dimethylamino)methylene]-β-oxo-benzenepropanenitrile is produced.

12. The process of claim 1, wherein α-[(dimethylamino)methylene]-3,4-dimethyl-β-oxo-benzenepropanenitrile is produced.

13. The process of claim 1, wherein 2,4-dichloro-α-[(dimethylamino)methylene]-β-oxo-benzenepropanenitrile is produced.

14. The process of claim 1, wherein α-[(dimethylamino)methylene]-2,6-difluoro-β-oxo-benzenepropanenitrile is produced.

15. The process of claim 1, wherein α-[(dimethylamino)methylene]-4-methyl-β-oxo-2-thiophenepropanenitrile is produced.

16. The process of claim 1, wherein α-[(dimethylamino)methylene]-1-methyl-β-oxo-1H-pyrrole-2-propanenitrile is produced..

17. The process of claim 1, wherein α-[(dimethylamino)methylene]-3-methyl-β-oxo-2-thiophenepropanenitrile is produced.

18. The process claim 1, wherein α-[(dimethylamino)methylene]-2,4-difluoro-β-oxo-benzenepropanenitrile is produced.

19. The process of claim 1, wherein α-[(dimethylamino)methylene]-2,5-difluoro-β-oxo-benzenepropan-enitrile is produced.

* * * * *

IN THE UNITED STATES PATENT AND TRADEMARK OFFICE

CERTIFICATE OF CORRECTION

PATENT NUMBER: 5,059,709

DATED: October 22, 1991

INVENTOR(S): John P. Dusza, Robert F. Church

It is certified that error appears in the above-identified patent and that said Letters Patent is hereby corrected as shown below:

In column 2, line 35, and in column 8, line 5, delete
"  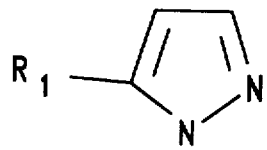  "   and insert --
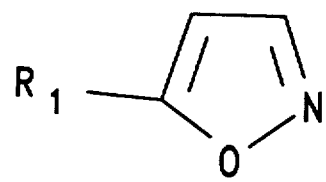
-- therefor.

Signed and Sealed this

Sixth Day of April, 1993

Attest:

STEPHEN G. KUNIN

Attesting Officer

Acting Commissioner of Patents and Trademarks